(12) United States Patent
Adamovich et al.

(10) Patent No.: US 12,157,920 B1
(45) Date of Patent: Dec. 3, 2024

(54) METHODS FOR DIAGNOSING AND ASSESSING DISEASE USING DRAIN FLUID

(71) Applicant: Droplet Biosciences, Inc., Cambridge, MA (US)

(72) Inventors: Wendy Winckler Adamovich, Melrose, MA (US); Seka Lazare, Boston, MA (US); Damion L. Whitfield, Cambridge, MA (US); Megan Elisabeth Long, Greenville, RI (US)

(73) Assignee: Droplet Biosciences, Inc., Cambridge, MA (US)

( * ) Notice: Subject to any disclaimer, the term of this patent is extended or adjusted under 35 U.S.C. 154(b) by 0 days.

(21) Appl. No.: 18/636,923

(22) Filed: Apr. 16, 2024

Related U.S. Application Data

(60) Provisional application No. 63/599,299, filed on Nov. 15, 2023.

(51) Int. Cl.
*C12N 15/10* (2006.01)
*C12Q 1/6886* (2018.01)

(52) U.S. Cl.
CPC ....... *C12Q 1/6886* (2013.01); *C12N 15/1013* (2013.01); *C12N 15/1093* (2013.01); *C12Q 2600/112* (2013.01)

(58) Field of Classification Search
CPC ............ C12N 15/1013; C12N 15/1093; C12Q 1/6886; C12Q 2600/112
See application file for complete search history.

(56) References Cited

U.S. PATENT DOCUMENTS

| | | | |
|---|---|---|---|
| 6,210,891 B1 | 4/2001 | Nyren et al. | |
| 6,306,597 B1 | 10/2001 | Macevicz | |
| 6,828,100 B1 | 12/2004 | Ronaghi | |
| 6,833,246 B2 | 12/2004 | Balasubramanian | |
| 6,911,345 B2 | 6/2005 | Quake et al. | |
| 7,232,656 B2 | 6/2007 | Balasubramanian et al. | |
| 7,598,035 B2 | 10/2009 | Macevicz | |
| 7,835,871 B2 | 11/2010 | Kain et al. | |
| 7,960,120 B2 | 6/2011 | Rigatti et al. | |
| 2006/0024681 A1 | 2/2006 | Smith et al. | |
| 2006/0292611 A1 | 12/2006 | Berka et al. | |
| 2007/0114362 A1 | 5/2007 | Feng et al. | |
| 2011/0009278 A1 | 1/2011 | Kain et al. | |

FOREIGN PATENT DOCUMENTS

WO    WO-2021127065 A1 * 6/2021    ............. A61K 45/06

OTHER PUBLICATIONS

BioDynami (cfDNA Purification Kit protocol) (Year: 2023).*
Meyer et al. (Cold Spring Harb Protoc; 2010; doi:10.1101/pdb.prot5448) (Year: 2010).*

* cited by examiner

*Primary Examiner* — Jeremy C Flinders
(74) *Attorney, Agent, or Firm* — Withers Bergman LLP; Thomas C. Meyers

(57) ABSTRACT

The present invention provides methods for using drain fluid obtained from medical procedures to assess diagnostic biomarkers indicative of disease obtained from drain fluid. In some embodiments, the diagnostics biomarkers are cell-free nucleic acids. In some embodiments, the disease is cancer. In some embodiments, a library of cfDNA is prepared and/or sequenced. In some embodiments, the methods comprise extracting nucleic acid from surgical drain fluid; conducting a size selection procedure to isolate cell-free nucleic acid from the surgical drain fluid; and detecting the cell-free nucleic acid.

7 Claims, 4 Drawing Sheets

METHODS FOR DIAGNOSING AND ASSESSING DISEASE USING DRAIN FLUID

TECHNICAL FIELD

This invention provides methods for diagnosing and assessing disease based on biomarkers identified from drain fluid.

BACKGROUND

Cancer is a leading cause of death globally. Early detection, while beneficial for most cancers, is often difficult. In part, this is because many cancers first develop without presenting any specific clinical symptoms, and diagnosis only occurs when the disease has reached a stage when it is difficult to treat.

Many cancer diagnostics have focused on liquid biopsy in blood or plasma for the detection of cell-free tumor DNA. Conventional cfDNA extraction kits are available, such as the MagMax cfDNA kit (Thermo Fisher). In general, blood is of high clinical interest because of its accessibility. Unfortunately, many of these methods lack sensitivity. One reason for that is that the analytes to be detected (e.g., cfDNA) are present in very small amounts in blood. As a result, early cancer detection is often difficult. Moreover, due to the lack of sensitivity, progression of the disease and its response to therapeutic intervention are difficult to monitor.

Tissue, such as tumor tissue, generally is the most informative sample for diagnosis and prognosis of cancer. Unfortunately, tissue samples are often difficult to access and subject to limited availability, especially without performing an invasive procedure. In the context of cancer, biopsy material often gives little indication of metastatic potential.

Consequently, physicians and patients are often unable to make timely, informed decisions regarding therapeutic intervention.

SUMMARY

The invention provides methods for using drain fluid (i.e., effluent) obtained from medical procedures (e.g., medical interventions such as surgeries, biopsies, catheterizations, dissections, intubations and the like) to assess diagnostic biomarkers indicative of disease. In one embodiment, the invention comprises methods for extraction and use of cfDNA in drain fluid. According to the invention, cfDNA is extracted using smaller input volumes and at significantly higher yields than would be possible in conventional isolation from drain fluid or plasma. Thus, in a preferred instance, the invention comprises extracting cfDNA from drain fluid and performing size selection to extract cfDNA from the sample. The size selection step may be performed any number of times as is suitable to obtain a desired yield. Use of methods disclosed and claimed herein results in a greater yield of extracted cfDNA than would be possible if conventional plasma-based assays are used on drain fluid. In addition to the extraction of cfDNA, methods of the invention can be applied to the extraction of other analytes, such as RNA and proteins.

In specific instances, the invention comprises extracting nucleic acid from a drain fluid, size selecting for cell-free nucleic acid, and detecting and/or identifying the size-selected nucleic acid. Certain embodiments of the invention comprise removing genomic DNA (gDNA) from the sample prior to, or simultaneously with, the size selecting step. In one example, beads, such as magnetic or paramagnetic beads, are used to remove the gDNA.

Methods of the invention are useful for isolating nucleic acid for diagnosis, prognosis, and assessment of disease (e.g., staging), as well as evaluating therapeutic selection and efficacy. The nucleic acids obtained via methods of the invention can be evaluated by sequencing methods and compared to wild-type or disease model sequences. In addition, a genomic profile created from nucleic acid obtained in the invention is useful to model disease progression. Libraries of, for example, cfDNA made using methods of the invention are useful for the evaluation of samples as well as for creation of a database for analysis of subsequent samples.

In preferred embodiments, the cfDNA is circulating tumor DNA (ctDNA). The ctDNA obtained as described herein can be sequenced and compared to profiles obtained from tumor biopsy samples, blood samples, and/or lymphatic samples. Thus, methods of the invention are useful to create multimodal genomic profiles that are used to track cancer progress, to detect minimal residual disease (MRD), and to predict recurrence and metastasis. Methods of the invention also may be used to yield quantitative information concerning cfDNA by, for example, amplifying extracted cfDNA using quantitative methods, such as qPCR.

Contrary to conventional thinking, drain fluid, usually considered biological "waste", is a rich source of diagnostic information. Moreover, drain fluids comprising fluid originating in lymphatics and as interstitial fluid is more representative of the biomarker heterogeneity of a tumor than would be obtained from a biopsy or blood sample. The information obtained from drain fluid is, therefore, informative for a diagnostic assay, whether performed on the obtained drain fluid or at a subsequent time in blood or downstream lymphatic fluid. In a preferred embodiment, the invention provides both the ability to create a more informative personalized array of biomarkers as well as the ability to perform longitudinal monitoring of individual patients to assess recurrence, minimal residual disease and response to treatment generally.

In general, drain fluid can be obtained as effluent from a medical intervention, such as a surgery or biopsy. Drain fluid can also be obtained during treatment of a wound or interventional procedure. Methods taught herein provide sensitive and specific diagnostics that allow assessment of disease status, staging, and progression; as well as aiding in therapeutic selection and assessment of therapeutic efficacy. As used herein, drain fluid does not imply only fluid obtained from a drain device, although that can be the case. Rather, drain fluid is intended to be fluid originating in the lymphatics and, in some cases, progressing via lymphatic channels to lymph glands and ultimately to blood. Drain fluid may comprise interstitial fluid and may be obtained as a mixture with other bodily fluids, including blood. A wash fluid or rinse may also be part of the drain fluid as obtained during a medical intervention. However, the invention is focused on diagnostic content in the drain fluid or effluent originating in vivo.

The present invention is useful for evaluation of any disease biomarker. However, in a preferred embodiment, drain fluid is a source of cell-free nucleic acid. In certain embodiments, the cell-free nucleic acid is DNA or RNA. In another embodiment, drain fluid is a source of circulating tumor DNA (ctDNA), tumor cells, ratios of ctDNA to cells, mutations associated with cancer, oncogenes and the like. The invention is also useful for the assessment of diseases other than cancer, including infectious diseases, autoimmune diseases, endocrine diseases and the like.

Accordingly, the present invention provides a method for disease diagnosis comprising the steps of obtaining a drain fluid sample, extracting nucleic acid from the sample, conducting a size selection procedure to isolate cell-free nucleic acid in the sample, and detecting the cell-free nucleic acid. In certain embodiments, methods of the invention further include sequencing the cell-free nucleic acid and (i) diagnosing and/or staging cancer and/or (ii) selecting or evaluating a therapeutic. In certain aspects, the cell-free nucleic acid is isolated without a prior step of extracting nucleic acid from the sample. The disease evaluated can be any disease, including cancer, infectious disease, metabolic disease or an autoimmune disease. However, the invention has particular application in the diagnosis, prognosis, and monitoring of cancer.

In a certain embodiment, the invention includes repeating the extracting step at least once. In another embodiment, methods include repeating the conducting step at least once. The cfDNA percentage and/or quantity may be assessed after each extraction or size selection round, and the extraction and/or size selection steps are repeated until the desired percentage and/or quantity of cfDNA is achieved. The desired percentage and/or quantity of cfDNA may correspond to a target detection threshold. In certain embodiments, the desired percentage of cfDNA is at least about 70%. In certain embodiments, the desired quantity of cfDNA is at least about 600 ng. The size selection rounds may comprise the addition of beads. In addition, the invention may further comprise treatment with Proteinase K prior to the addition of beads.

According to the invention, conventional plasma cfDNA extraction kits are not suitable as the sole extraction method for cfDNA in surgical drain fluid. Surgical drain fluid differs in many aspects from plasma, including the presence of a high concentrations of cfDNA as well as genomic DNA. The present invention provides methods in which cfDNA isolation is enhanced through the combination of extraction and size exclusion. The present invention further provides methods direct isolation of cfDNA from drain fluid without the need for a prior nucleic acid extraction step. Such methods include steps to minimize gDNA include bead purification to size select the DNA fragments in a cfDNA sample. In some embodiments, bead purification comprises magnetic beads. In some embodiments, the ratio of beads to the drain fluid can be about 0.1×, 0.2×, 0.3×, 0.4×, 0.5×, 0.6×, 0.7×, 0.8×, 0.9×, or 1×.

The present invention also provides methods of library preparation from surgical drain fluid. Libraries prepared from cfDNA in surgical drain fluid are informative for disease status, such as, for example, cancer status. The cfDNA concentration in the surgical drain fluid is assessed, for example, by electrophoresis (e.g. TapeStation System, Agilent, and/or Bioanalzyer, Agilent), and used to determine the volume of surgical drain fluid necessary for library preparation. Then, the cfDNA from the surgical drain fluid is subject to a buffer exchange procedure followed by end repair, A-tailing, ligation of barcodes e.g. non-random unique molecular identifiers (UMIs), ligation of adaptors, and followed by PCR amplification. The buffer exchange procedure may comprise a size selection procedure. Once prepared, the sequencing library or a portion thereof can be sequenced to obtain a plurality of sequence reads. The sequence reads may be in a computer-readable, digital format for processing and interpretation by computer software. Such libraries in some instances provide enhanced accuracy for diagnosing diseases or conditions and are substantially free of biological contamination.

In another aspect, methods of the present invention contemplate creating a genomic profile from DNA or RNA in the drain fluid. In another aspect, a genomic profile may be created from DNA or RNA in plasma and compared to a genomic profile from DNA or RNA in the drain fluid. Additionally, a genomic profile may be created from DNA or RNA in a tumor biopsy sample and compared to a genomic profile from DNA or RNA in the drain fluid.

DETAILED DESCRIPTION

Figure 1:
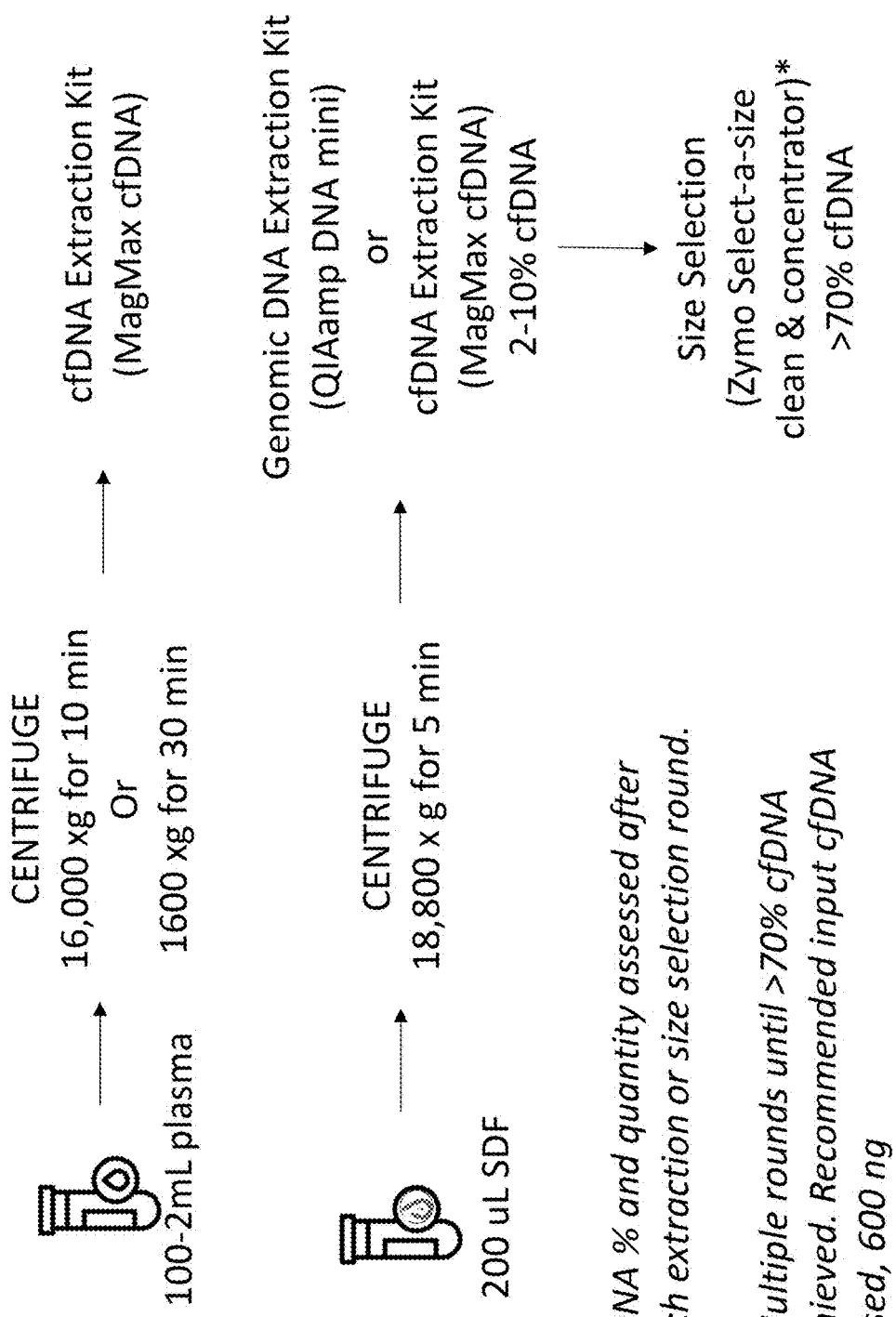
FIG. 1 shows a workflow comparison between conventional cfDNA extraction from plasma and methods of the invention.

The present invention provides methods for using drain fluid (i.e., effluent) obtained from medical procedures (e.g., medical interventions such as surgeries, biopsies, catheterizations, dissections, intubations and the like) to assess diagnostic biomarkers indicative of disease.

According to the invention conventional plasma cfDNA extraction methods are not suitable and are ineffective as the sole extraction method for cfDNA from drain fluid. Instead, cfDNA from drain fluid is subjected to a separate size exclusion step after extraction.

Drain fluid for use in the invention may be obtained by any known method. For example, the drain fluid may be obtained passively as the effluent from a medical procedure. Alternatively, one may use a catheter or a drain port for actively or passively collecting fluid. Suction drainage, for example using a vacuum, may also be used to obtain fluids during a surgical procedure. The surgical drain fluid may be collected by using a syringe, pipet, or catheter, for example a Jackson-Pratt (JP) drain. The drain fluid may be collected in or transferred to a container, for example a sample vessel, such as a vial, flask, or ampule, suitable for the sterile collection of medical specimens. Surgical fluid may also be collected from biohazard waste containers, for example a suction canister, filled during a procedure or diverted from a biohazard waste container during a surgical procedure. Sample may be obtained by irrigating a surgical wound. Irrigating fluid may comprise water, saline, antibiotic solutions, antiseptic agents, or a combination thereof.

Surgical drain fluid may be collected from any surgical procedure. For example, the surgery may comprise an open surgical procedure or an endoscopic procedure. The surgical procedure may comprise an invasive procedure. The surgical procedure may comprise a resection, biopsy, dissection, or excision. The surgical procedure may be a thoracentesis. The surgical procedure may be a minimally invasive procedure, such as, for example, a stent placement. The surgical procedure may be a procedure that is not a related to a disease being diagnosed. Thus, the invention applies to any disease condition and the drain fluid may be from an unrelated interventional procedure. Drain fluid may be obtained at any time during or following an interventional procedure. For example, drain fluid may be collected at the time of intervention and then periodically over the course of hours, days or weeks.

As discussed above, surgical drain fluids have high genomic content. Methods to minimize gDNA contamination include bead purification to size select the DNA fragments in a cfDNA sample. In some embodiments, isolating cfDNA is done in such a manner as to maximize the recovery of short fragments (<100 base pairs), as the composition of short fragments differs more between healthy and disease states than the composition of longer fragments. In some embodiments, the cfDNA fragments are subjected to a size selection to retain only cfDNA fragments having a length between an upper bound and a lower bound. In some embodiments, the upper bound is about 200, about 190, about 180, about 170, about 160, about 150, about 140, about 130, about 120, about 110, about 100, about 90, about 80, about 70, about 60, or about 50 base pairs and the lower bound is about 20, about 25, about 30, about 35, about 36, about 40, about 45, about 50, about 60, about 70, about 80, about 90, about 100, about 110, or about 120 base pairs. In some embodiments, the lower bound is 36 and the upper bound is 100. In some embodiments, the beads are magnetic beads. In some embodiments, the ratio of beads to the drain fluid can be 0.1×, 0.2×, 0.3×, 0.4×, 0.5×, 0.6×, 0.7×, 0.8×, 0.9×, and 1×. In some embodiments, the ratio of magnetic beads may be added in staggered steps, e.g., where 0.4× beads are added, and then separated and an additional 0.1× beads is added to the supernatant.

In various aspects, cfDNA may be identified and quantified using methods known in the art. Suitable assays include, for example, nucleic acid sequencing, PCR, quantitative PCR, digital and droplet PCR. Sequencing may be performed by various methods known in the art. For example, see, generally, Quail, et al., 2012, A tale of three next generation sequencing platforms: comparison of Ion Torrent, Pacific Biosciences and Illumina MiSeq sequencers, BMC Genomics 13:341. Nucleic acid molecule sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Tumor-informed plasma-based cfDNA assays for detection of minimal residual disease (MRD) after cancer treatment are limited by 1) sampling bias from a small sampling of the tumor, and 2) tumor heterogeneity and subclonality that develops during the course of carcinogenesis and metastasis. As discussed above, according to the invention, surgical drain fluid in patients undergoing cancer surgery is a good source of tumor cfDNA. The characterization and/or quantification of tumor cfDNA in the surgical drain fluid is useful to measure locoregional minimal residual disease as well as for determining the risk of recurrence. Additionally, cfDNA in drain fluid broadly captures tumor heterogeneity in a manner that is difficult or impossible with the small biopsy sample typically obtained from primary tumor tissue. Thus, drain fluid allows detection of a broader spectrum of variants, including high-risk variants, that represent the entirety of the tumor and lymph nodes metastases. Methods described herein increase the yield of informative cfDNA from tumor sources.

In yet another aspect, the invention provides methods for determining MRD. Tumor DNA extracted using methods of the invention is sequenced and informative or potentially-informative variants are determined. The cfDNA is used to design a customized MRD panel that is then used to monitor the patient for recurrence, disease progression, response to treatment and other clinical signs over a period of time at the discretion of the clinician.

An advantage of this aspect of the invention is that a panel constructed, at least in part, from cfDNA variants obtained in drain fluid allows for personalized surveillance monitoring of a patient. As discussed above, variant panels based on drain fluid incorporates variants that may be missing in tumor biopsy which, by definition, may not be representative of overall tumor heterogeneity. As an example, a biopsy may capture about 1 mm of, for example, a 5 cm tumor. Thus, any variants not captured in that sample will not be included in any subsequent analysis. Drain fluid provides a more representative sample of the heterogeneity of a tumor, as drain fluid is not confined to only a portion of the tumor. Thus, an assay panel based on drain fluid provides a representative and more informative assessment of tumor heterogeneity, which allows for more precision in patient longitudinal monitor.

Methods of the invention are also useful to construct a blood-based panel for assessment of therapeutic efficacy. In this aspect, a panel created, at least in part, based on cfDNA in drain fluid is used to establish a baseline and then to monitor the patient through a course of treatment to determine the effect of the treatment on reducing the presence of tumor-associated cfDNA over time as a proxy for successful treatment of the primary tumor and/or metastasis.

Methods of the invention also contemplate assessment of pharmaceutical efficacy. According to the invention, accumulation of ctDNA in drain fluid after therapy is indicative that the therapy is effective, as an increase in tumor DNA in drain fluid after therapy is indicative of the induction of cell death in the tumor. Thus, real-time measurement during therapy is indicative of therapeutic efficacy. According to methods of the invention the rate of accumulation or decrease of cfDNA in drain fluid is indicative of disease severity and whether a disease is progressing or regressing. For example, if drain fluid is measured at multiple time points, it is possible to calculate a slope of cfDNA accumulation. The slope is indicative of the velocity of change (either negative or positive). In the same way, the area under the curve resulting from multiple measurements in the drain fluid is indicative of disease progression or regression.

FIG. 1 shows a comparison of workflow in a conventional plasma-based assay for cfDNA and methods of the invention. As noted in the Figure and above, methods of the invention comprises a size selection step that increases the yield of cfDNA. To achieve maximum effect, multiple rounds of extraction may be conducted.

Figure 2A:
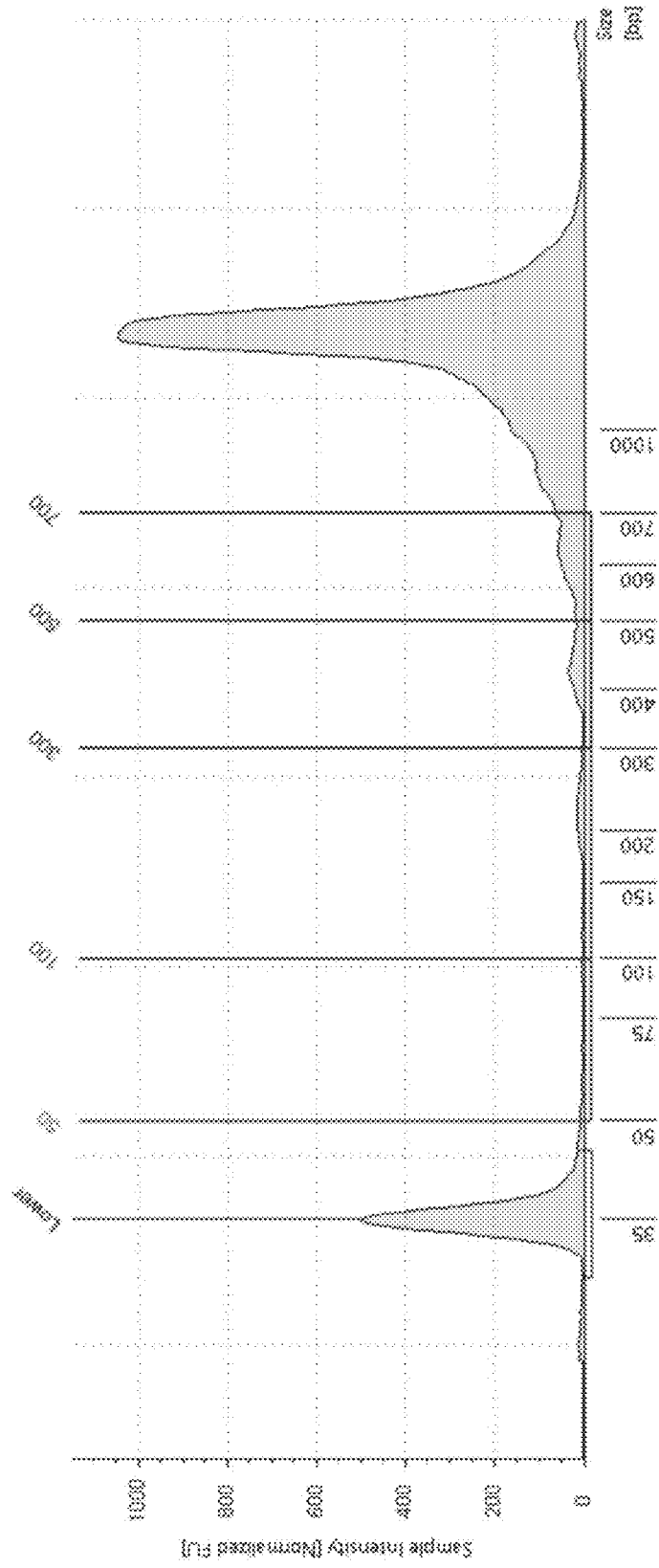
FIGS. 2A-2C show results of a comparison of methods of the invention with conventional methods.
Figure 2B:
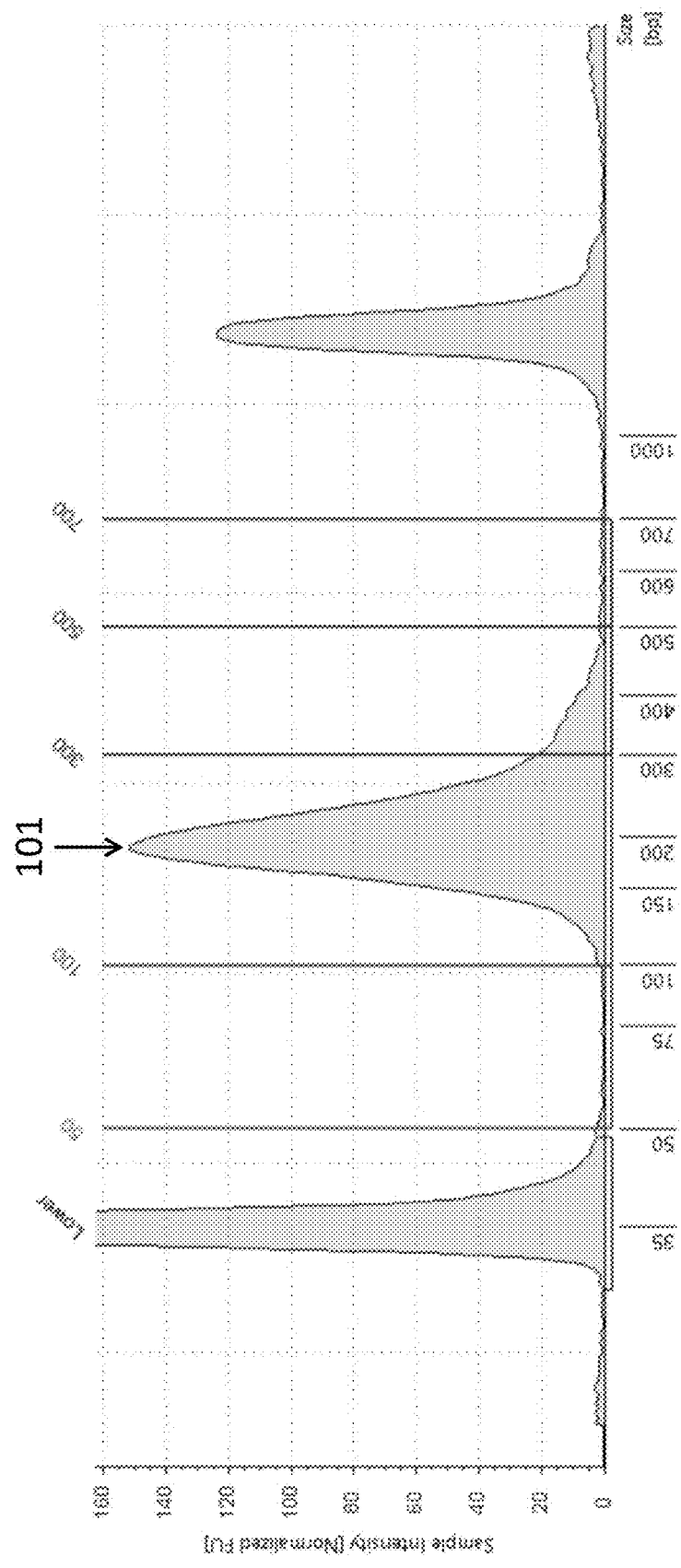
Figure 2C:
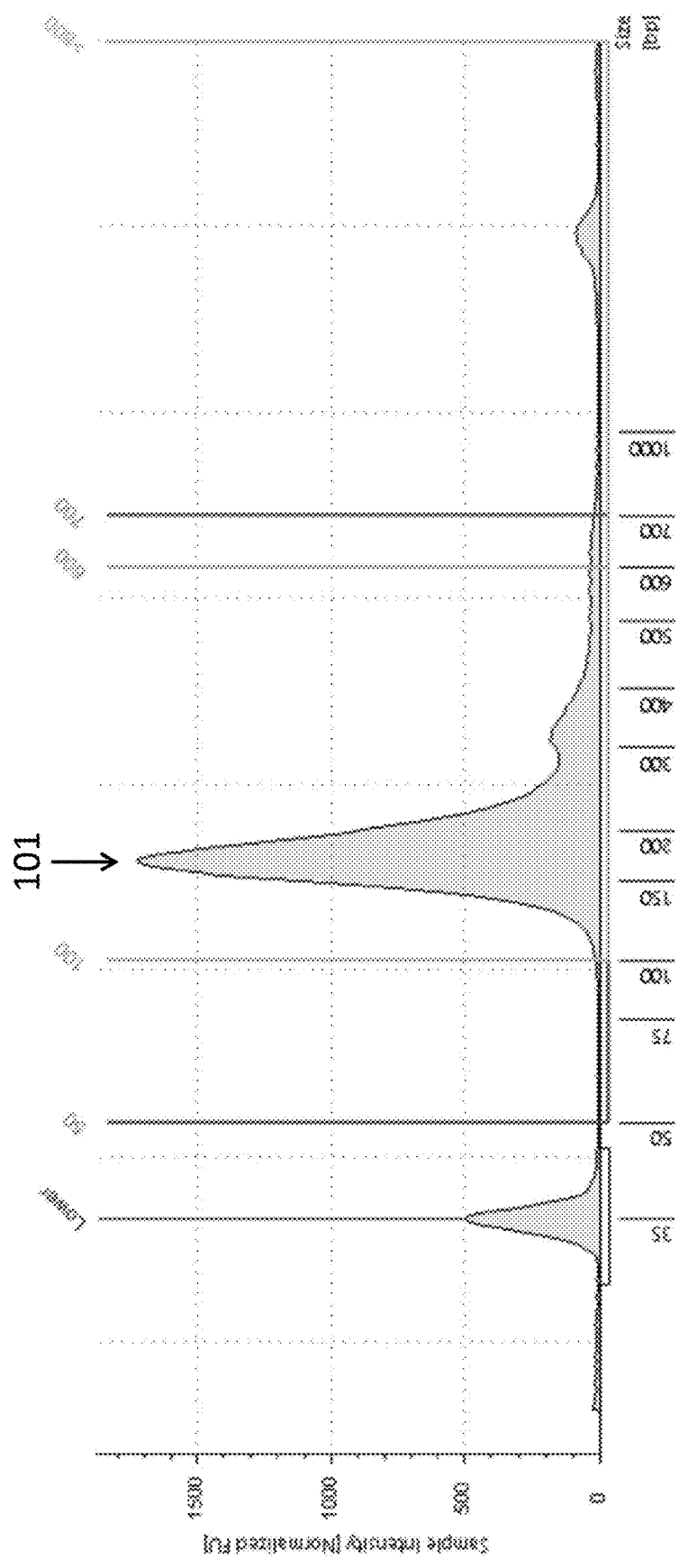

FIGS. 2A-2C shows results of cfDNA extraction in SDF with and without size selection versus plasma extraction. As shown in the Figure, cfDNA extraction followed by size selection in SDF (FIG. 2A) reveals a cfDNA fraction 101 not seen using conventional cfDNA extraction in the SDF (FIG. 2B). For comparison, results of conventional cfDNA extraction in plasma are shown in FIG. 2C, where the cfDNA fraction 101 is revealed.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for isolating cell-free nucleic acid, the method comprising the steps of:
   treating a drain fluid sample with proteinase K;
   introducing, subsequent to the treating step, beads to the drain fluid sample;
   repeating the introducing step at least once, thereby to size-select for cell-free nucleic acid; and
   detecting the cell-free nucleic acid.

2. The method of claim 1, wherein the beads are paramagnetic beads.

3. The method of claim 1, wherein the cell-free nucleic acid in the detecting step is at least about 600 ng.

4. The method of claim 1, wherein the drain fluid sample is obtained from a surgical procedure.

5. The method of claim 1, wherein the drain fluid is obtained at a time subsequent to a surgical procedure.

6. The method of claim 1, wherein the cell-free nucleic acid is DNA.

7. The method of claim 6, wherein the DNA is present as fragments from about 50 to about 200 nucleotides in length.

* * * * *